United States Patent
Dumont

(10) Patent No.: US 11,541,155 B2
(45) Date of Patent: Jan. 3, 2023

(54) CLOSED AND STERILE CONTAINER DEVICES FOR CRYOPRESERVATION AND RESUSPENSION OF BODY FLUIDS

(71) Applicant: Vitalant, Scottsdale, AZ (US)

(72) Inventor: Larry J. Dumont, Aurora, CO (US)

(73) Assignee: Vitalant, Scottsdale, AZ (US)

( * ) Notice: Subject to any disclaimer, the term of this patent is extended or adjusted under 35 U.S.C. 154(b) by 755 days.

(21) Appl. No.: 16/423,650

(22) Filed: May 28, 2019

(65) Prior Publication Data

US 2019/0365969 A1  Dec. 5, 2019

Related U.S. Application Data

(60) Provisional application No. 62/678,765, filed on May 31, 2018.

(51) Int. Cl.
*A61M 1/02* (2006.01)
*A01N 1/02* (2006.01)

(52) U.S. Cl.
CPC .......... *A61M 1/0281* (2013.01); *A01N 1/021* (2013.01); *A61M 2202/0415* (2013.01); *A61M 2202/0427* (2013.01)

(58) Field of Classification Search
None
See application file for complete search history.

(56) References Cited

U.S. PATENT DOCUMENTS

| | | | |
|---|---|---|---|
| 4,596,657 A | 6/1986 | Wisdom | |
| 4,994,057 A | 2/1991 | Carmen et al. | |
| 5,858,642 A | 1/1999 | Cain et al. | |
| 5,879,318 A | 3/1999 | Van Der Heiden et al. | |
| 7,618,584 B2 | 11/2009 | Lampeter et al. | |
| 8,633,023 B2 * | 1/2014 | Du | A01N 1/0236 435/325 |
| 10,271,543 B2 * | 4/2019 | Woods | A01N 1/0231 |
| 10,279,097 B2 | 5/2019 | Meisberger et al. | |
| 10,589,008 B2 | 3/2020 | Schmidt et al. | |
| 10,632,476 B2 | 4/2020 | Meisberger et al. | |
| 2003/0031998 A1 | 2/2003 | Kadkade | |
| 2004/0097862 A1 | 5/2004 | Lampeter et al. | |
| 2010/0281886 A1 * | 11/2010 | Shaham | A01N 1/0263 62/51.1 |
| 2012/0219633 A1 | 8/2012 | Sowemimo-Coker | |
| 2015/0113919 A1 * | 4/2015 | Provitera | B29C 66/1122 53/440 |
| 2018/0315501 A1 | 11/2018 | Remondi | |
| 2019/0194597 A1 | 6/2019 | Harada et al. | |

FOREIGN PATENT DOCUMENTS

| | | |
|---|---|---|
| JP | 2004-532053 | 10/2004 |
| RU | 167874 | 11/2017 |
| WO | WO 02/065976 | 8/2002 |
| WO | WO 2008/035240 | 3/2008 |

OTHER PUBLICATIONS

Mitrus I. et al. Comparison of 5% Albumin and Autologous Plasma Used for Cryopreservation of Peripheral Blood Progenitor Cells. Bone Marrow Transplantation 49(Suppl 1)S530 Mar. 2014. (Year: 2014).*
Clarke D. et al. Cryopreservation Formulations and Container Systems Designed to Improve Storage and Transport of Cell and Gene Therapies. Molecular Therapy 26(5, Suppl 1)82/174 May 2018. (Year: 2018).*
Zhang, X. et al. A Dialysis Washing System for Removal of Cryoprotective Agent . . . Int Congress of Refrigeration 22nd Meeting Aug. 21-26, 2007. (Year: 2007).*
Johnson et al., "PAS-G supports platelet reconstitution after cryopreservation in the absence of plasma," *Transfusion*, Oct. 2013, vol. 53, pp. 2268-2277.
Bohoněk, "Cryopreservation of Platelets: Advances and Current Practice," Cryopreservation Biotechnology in Biomedical and Biological Sciences, IntechOpen, Dec. 7, 2018, 24 pages.

* cited by examiner

*Primary Examiner* — Ralph J Gitomer
(74) *Attorney, Agent, or Firm* — Polsinelli PC

(57) ABSTRACT

The disclosure provides for a container system and method for the cryopreservation and resuspension of a body fluid. The container system may include a cryopreservation container comprising the body fluid in a cryopreservation liquid, a resuspension container comprising a resuspension solution, a connection tube sterilely connecting the cryopreservation container and the resuspension container, and at least one shut-off element actively associated with the connection tube.

11 Claims, 4 Drawing Sheets

CLOSED AND STERILE CONTAINER DEVICES FOR CRYOPRESERVATION AND RESUSPENSION OF BODY FLUIDS

CROSS-REFERENCE TO RELATED PATENT APPLICATION

This patent application claims the benefit under 35 U.S.C. § 119(e) of U.S. Patent Application Ser. No. 62/678,765, entitled "METHODS AND SYSTEMS FOR CRYOPRESERVATION AND RESUSPENSION OF BODY FLUIDS," filed on May 31, 2018, which is incorporated herein by reference in its entirety.

FIELD

The present disclosure is directed to a cryopreservation and resuspension system for body fluids and methods of use thereof.

BACKGROUND

Blood products and other body fluids or biologicals may be cryopreserved for long term storage. The preparation of the product for freezing may be in a manner to prevent contamination of the product, for example with aseptic handling and filling operations or through the use of sterile connection devices. After the product is thawed through any variety of means, e.g. water bath, the product must be prepared for administration/transfusion which may require dilution, washing, centrifugation, filtration, resuspension or similar steps that require accessing the product storage container. These processes may breach the closed system of the storage container, and therefore subject the product to potential contamination.

This presents an increased risk to the product and the patient, and limits the time interval between preparation and administration/transfusion to 4-6 hours depending on the regulatory jurisdiction. These operations could be performed in a validated aseptic handling environment (i.e., clean room). However, many locations of final use do not have the validated facilities and trained personnel to aseptically process in a controlled environment (e.g., some hospitals, rural health care settings, home settings, remote emergency care, or austere environments such as military deployment zone). Functionally closed operations may be facilitated by the use of sterile tube welding. But, some freezing storage systems are not conducive to a device design/material selection that will permit compatibility to approved sterile connection devices.

For example, conventional resuspension operations necessitate breaching the storage container may result in a 4-6 hour expiry time for the thawed cells, such as cryopreserved platelets (CPP). This can result in waste of valuable product if the product is not administered to the patient within that time window.

Accordingly, there remains a need in developing a system and method for freezing, resuspending body fluids in a closed system such that the contents of the system remain sterile through thawing, resuspension, and storage until used by a patient.

BRIEF SUMMARY

The disclosure provides for container systems and methods of use thereof. In one aspect, the container system includes a cryopreservation container having a body fluid in a cryopreservation liquid, a resuspension container with a resuspension solution, a connection tube sterilely connecting the cryopreservation container and the resuspension container, and at least one shut-off element actively associated with the connection tube. The body fluid may be selected from platelets and blood. When the container system is frozen, the shut-off element is closed such that the body fluid in the cryopreservation liquid and the resuspension solution cannot mix. The frozen container system may be thawed, the shut-off element is opened, and at least a portion of the resuspension solution is added to the cryopreservation container, creating a resuspended body fluid product. The resuspended body fluid product may remain shelf stable for more than 4 hours. The resuspension solution is a transfusable solution, such as sterile NaCl, human plasma, or a platelet storage solution. The container system may be a closed and sterile system.

In another aspect, the container system may include a cryopreservation container comprising a body fluid in a cryopreservation liquid, and a sterile filter sterilely and fluidly connected to the cryopreservation container. The container system may further include a resuspension container comprising a resuspension solution configured to connect to the sterile filter. A body fluid product may be created in the container system by thawing the cryopreservation container, connecting the resuspension container to the sterile filter, and adding at least a portion of the resuspension solution to the body fluid, creating a resuspended body fluid product. The resuspended body fluid product may remain shelf stable for more than 4 hours. The body fluid may be selected from platelets and blood. The resuspension solution may be a transfusable solution, such as sterile NaCl, human plasma, or a platelet storage solution. The container system may be a closed and sterile system.

In an aspect, a method of resuspending a cryopreserved body fluid may include thawing a frozen container where the shut-off element is closed such that the body fluid in a cryopreservation liquid and resuspension solution cannot mix, opening the shut-off element, and adding at least a portion of the resuspension solution to the cryopreservation container to create a resuspended body fluid product. The method may further include transporting the resuspended body fluid product to a site for transfusion. The resuspended body fluid product may be shelf stable for more than 4 hours. The resuspension solution may be a transfusable solution, such as sterile NaCl, human plasma, or a platelet storage solution. The method maintains the container system as a closed and sterile system.

In another aspect, a method of resuspending a cryopreserved body fluid may include thawing a frozen container system, connecting a resuspension container comprising a resuspension solution to the sterile filter; and adding at least a portion of the resuspension solution to the cryopreservation container to create a resuspended body fluid product. The method may further include transporting the resuspended body fluid product to a site for transfusion. The resuspended body fluid product is shelf stable for more than 4 hours. The resuspension solution may be a transfusable solution, such as sterile NaCl, human plasma, or a platelet storage solution. The method maintains the container system as a closed and sterile system.

Additional variations and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

The description will be more fully understood with reference to the following figures and data graphs, which are presented as variations of the disclosure and should not be construed as a complete recitation of the scope of the disclosure, wherein.

DETAILED DESCRIPTION

The disclosure may be understood by reference to the following detailed description, taken in conjunction with the drawings as described below. It is noted that, for purposes of illustrative clarity, certain elements in various drawings may not be drawn to scale.

Figure 1:
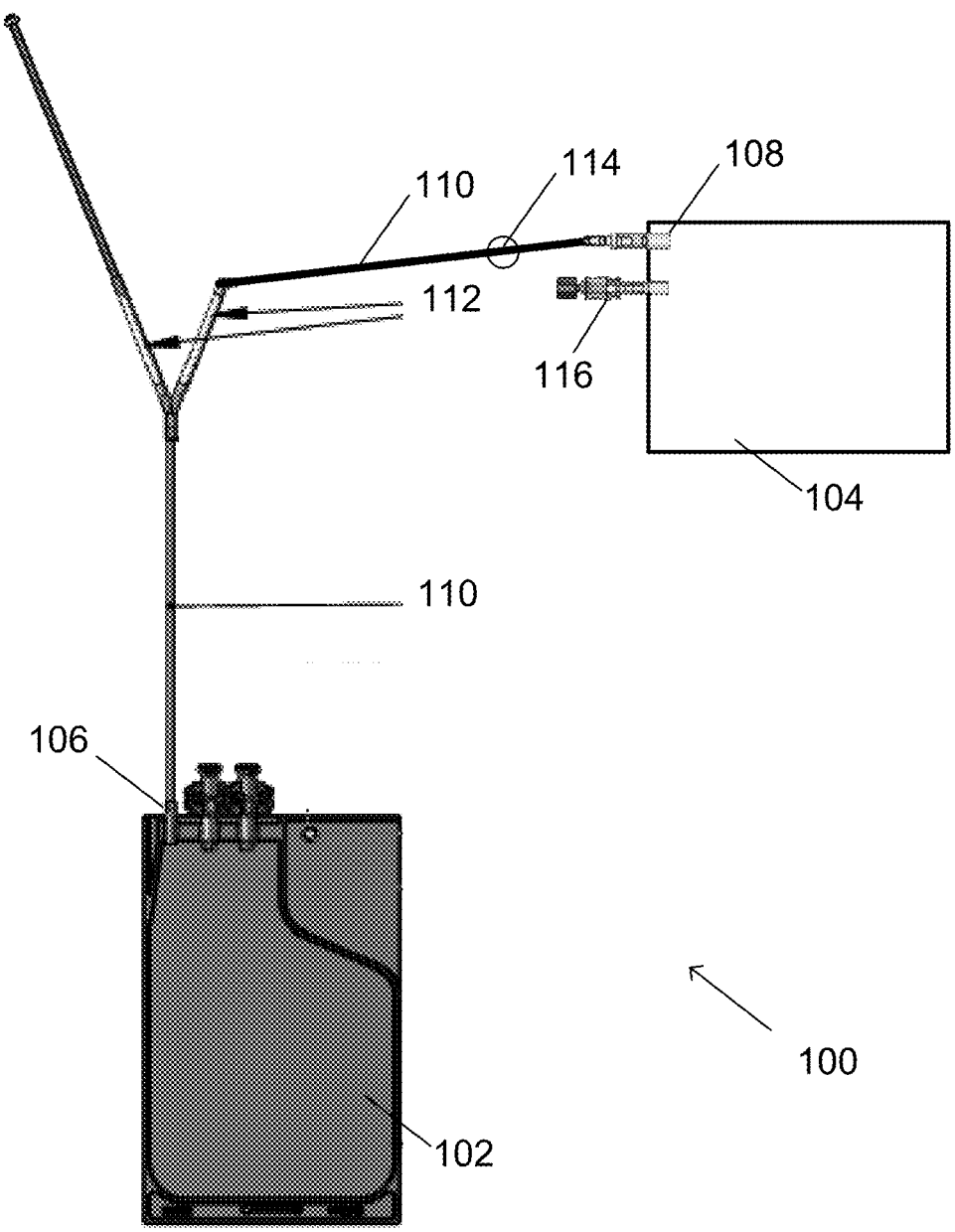
FIG. 1 is an illustration of the container system in one variation.
Figure 2:
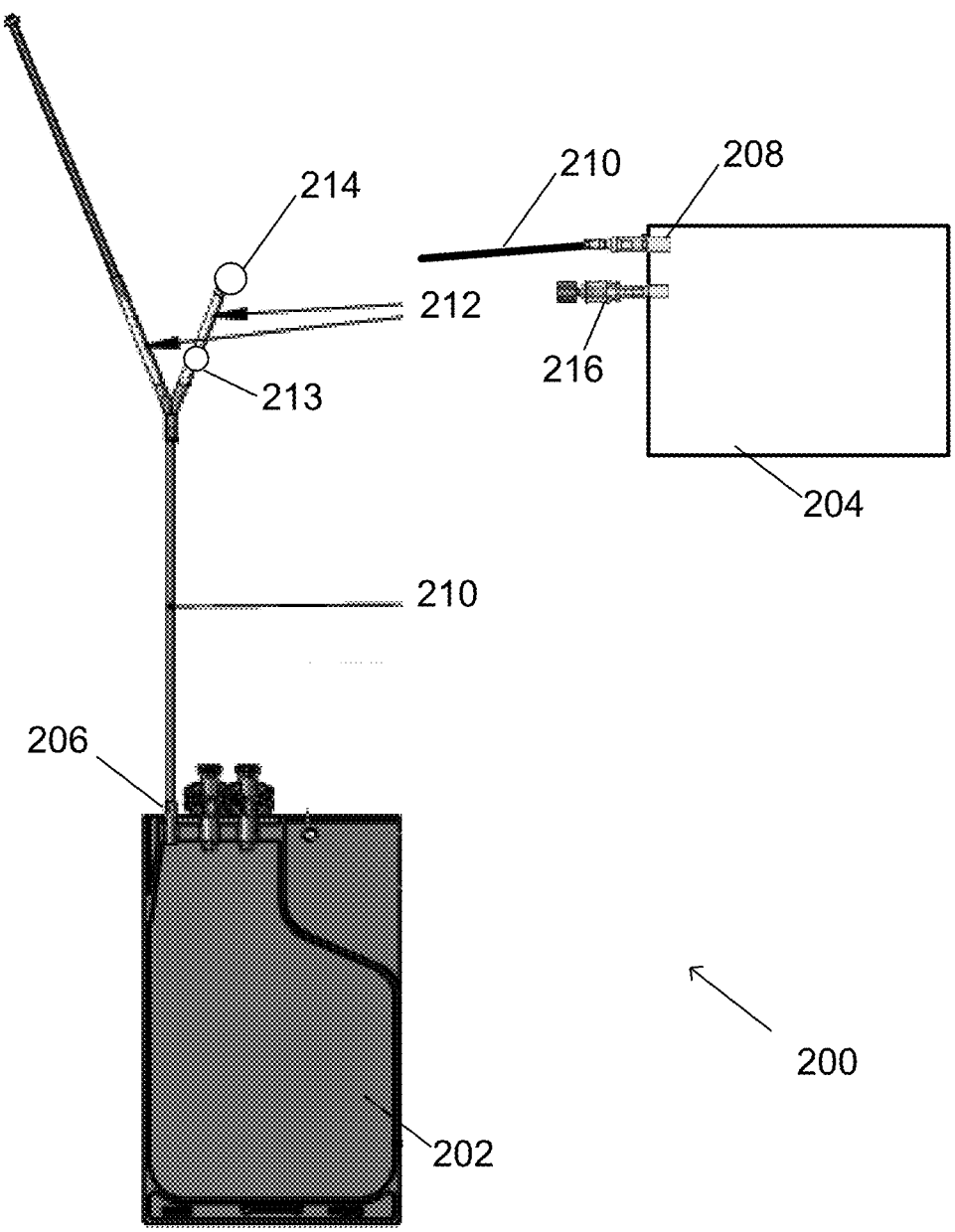
FIG. 2 is an illustration of the container system in one variation.

Disclosed herein are container systems and methods for the cryopreservation and resuspension of a body fluid. In one variation, as seen in FIG. 1, the container system may include a cryopreservation container, a resuspension container, a connection tube sterilely connecting the cryopreservation container and the resuspension container, and at least one shut-off element actively associated with the connection tube. The container system may be frozen together for up to 2 to 10 years depending on the body fluid. In another variation, as seen in FIG. 2, the container system includes a cryopreservation container and a sterile filter sterilely and fluidly connected to the cryopreservation container. This container system may further include a resuspension container configured to connect to the sterile filter after thawing.

The systems do not require a sterile connection/tube welding post thawing and do not require a validated, controlled environment for aseptic filling or sterilization operations. With the use of the systems with appropriate solutions, the final thawed and prepared body fluid product can be maintained for an extended period of time under appropriate conditions to aid in the treatment logistics. The system may prevent loss of body fluid product because the thawed and resuspended body fluid product may be sterile and stable for use more than 4-6 hours post preparation. For example, platelets resuspended using the container systems described herein may have a shelf life of greater than 4 hours up to at least 14 days. Other resuspended body fluids may have a shelf life of at least 3 months.

The thawed and prepared body fluid product can also be transported to the site of treatment under appropriate conditions. Non-limiting examples of treatment sites include transfusion services at hospitals, first responders in ambulances or helicopters, medical transportation and evacuation carriers, first responders on ground operations such as special forces. The extended shelf life may be important for civilian applications and military application. By extending the expiry time following thawing, the logistical preparation challenges are greatly relieved, reducing wastage, and permitting movement of the product to the site of care which could be remote from the site of storage and preparation. The thawed body fluid may be used to treat a patient in need of the body fluid. In one example, thawed CPP within the container system may be used treatment of acute hemorrhage in patients with a platelet deficiency or a platelet dysfunction.

Container System with Two Sterile Connected Containers

Provided herein is a container system for the cryopreservation and resuspension of a body fluid. As seen in FIG. 1, the container system 100 includes a cryopreservation container 102, a resuspension container 104, a connection tube 110 sterilely connecting the cryopreservation container and the resuspension container, and at least one shut-off element 114 actively associated with the connection tube.

The system includes a resuspension container pre-attached to a cryopreservation or freezing container prior to freezing such that a closed container system is available to thaw and prepare a body fluid product for administration/transfusion. The container system is prepared dry and sterilized by any manner of validated methods including but not limited to ethylene oxide, electron beam, gamma irradiation to form a sterile assembly.

The cryopreservation container 102 may be any container capable of holding a frozen body fluid. The cryopreservation container may be pliable or rigid. Non-limiting examples of materials that may compose the cryopreservation container include ethyl vinyl acetate (EVA), polyvinylchloride (PVC), polytetrafluoroethylene (PTFE), polyolefin polymers, such as polyethylene, and combinations thereof. In one variation, the cryopreservation container may be a cryopreservation bag. The cryopreservation bag is compatible with a cryopreservation fluid. For example, the cryopreservation bag is dimethyl sulfoxide (DMSO) compatible. In a variation, the cryopreservation container may be EVA freezing bag.

The cryopreservation container 102 may have one or more sterile connectors fluidly connected to the container. In a variation, the cryopreservation container includes at least 1 sterile connector. In a variation, the cryopreservation container includes at least 2 sterile connectors. In a variation, the cryopreservation container includes at least 3 sterile connectors. The sterile connectors may provide for sterilely connecting other containers to the cryopreservation container such that the contents of one container may be sterilely transferred to another container. The sterile connectors permit sterile welding of tubing for fluid transfers and/or connections for aseptic filling of fluids. In a variation, the sterile connectors are DMSO compatible. The cryopreservation container may have a volume sufficient to hold a desired amount of body fluid for transfusion. In a variation, the cryopreservation container may have a volume of at least 1 mL. In a variation, the cryopreservation container may have a volume of at least 5 mL. In a variation, the cryopreservation container may have a volume of at least 10 mL. In a variation, the cryopreservation container may have a volume of at least 25 mL. In a variation, the cryopreservation container may have a volume of at least 100 mL. In a variation, the cryopreservation container may have a volume of at least 200 mL. In a variation, the cryopreservation container may have a volume of at least 500 mL. In a variation, the cryopreservation container may have a volume of at least 800 mL. In a variation, the cryopreservation container may have a volume of at least 1000 mL.

The cryopreservation container contains a body fluid in a cryopreservation liquid. In a variation, the body fluid is added to the cryopreservation container though sterile tubing welds or other aseptic methods of transferring fluids. Non-limiting examples of body fluids that may be contained within the cryopreservation container include platelets, whole blood, red blood cells, plasma, cord blood, stem cells, mesenchymal stromal/stem cells, other biologicals, and/or combinations thereof. The body fluid may be human or animal body fluid for use in humans or animals. In one variation, the body fluid is platelets in plasma that have been collected from healthy volunteer allogeneic donors. The body fluid may be sterilized, if required. In a variation, collected platelets may be irradiated with 25Gy.

In a variation, the body fluid is combined with a cryopreservation fluid in the cryopreservation container. The cryopreservation fluid may be added to the body fluid aseptically in a clean room (e.g., ISO 5 classified) or using sterile welding of a cryopreservation fluid container to the cryopreservation container containing the body fluid. Examples of the cryopreservation fluid include DMSO, glycerol, or any fluid capable of preserving a frozen body fluid. In one variation, the cryopreservation fluid is 27% DMSO. In one variation, the body fluid mixture is DMSO cryopreserved platelets (CPP).

The cryopreservation fluid may be added such that it is 3% to 10% by volume of the total mixture. In a variation, the cryopreservation fluid may be at least 3% by volume of the mixture with the body fluid. In a variation, the cryopreservation fluid may be at least 6% by volume of the mixture with the body fluid. In a variation, the cryopreservation fluid may be at least 8% by volume of the mixture with the body fluid. In a variation, the cryopreservation fluid may be at least 10% by volume of the mixture with the body fluid. In another variation, the cryopreservation fluid may be less than or equal to 3% by volume of the mixture with the body fluid. In another variation, the cryopreservation fluid may be less than or equal to 6% by volume of the mixture with the body fluid. In another variation, the cryopreservation fluid may be less than or equal to 8% by volume of the mixture with the body fluid. In another variation, the cryopreservation fluid may be less than or equal to 10% by volume of the mixture with the body fluid.

After the cryopreservation fluid is added to the body fluid, the mixture may be concentrated within the cryopreservation bag, such as by centrifugation. The supernatant may then be removed from the cryopreservation bag so that the volume of the body fluid mixture in the cryopreservation bag is less than the starting volume of the body fluid and cryopreservation fluid. In a variation, the volume of concentrated body fluid mixture to be frozen is at least 1 mL. In a variation, the volume of concentrated body fluid mixture to be frozen is at least 5 mL. In a variation, the volume of concentrated body fluid mixture to be frozen is at least 10 mL. In a variation, the volume of concentrated body fluid mixture to be frozen is at least 15 mL. In a variation, the volume of concentrated body fluid mixture to be frozen is at least 20 mL. In a variation, the volume of concentrated body fluid mixture to be frozen is at least 25 mL. In a variation, the volume of concentrated body fluid mixture to be frozen is at least 35 mL. In a variation, the volume of concentrated body fluid mixture to be frozen is at least 50 mL. In a variation, the volume of concentrated body fluid mixture to be frozen is at least 100 mL. In other variations the volume of concentrated body fluid mixture to be frozen is less than or equal to 20 mL. In other variations the volume of concentrated body fluid mixture to be frozen is less than or equal to 25 mL. In other variations the volume of concentrated body fluid mixture to be frozen is less than or equal to 35 mL. In other variations the volume of concentrated body fluid mixture to be frozen is less than or equal to 50 mL. In other variations the volume of concentrated body fluid mixture to be frozen is or less than or equal to 100 mL. For example, platelets may be concentrated to 20 mL to 35 mL by centrifugation in the cryopreservation container.

The container system 100 further includes a resuspension container 104 having a resuspension solution contained within the resuspension container. The resuspension container may be any container capable of being frozen. The resuspension container may be pliable or rigid. Non-limiting examples of materials that may compose the resuspension container include EVA, PVC, PTFE, polyolefin polymers, such as polyethylene, and combinations thereof. In one variation, the resuspension container may be a bag. The resuspension bag may be compatible with the cryopreservation fluid. For example, the resuspension bag is DMSO compatible. In a variation, the cryopreservation container may be an EVA freezing bag.

The resuspension container 104 may have one or more sterile connectors 108 fluidly connected to the container. In a variation, the resuspension container includes at least 1 sterile connector. In a variation, the resuspension container includes at least 2 sterile connectors. In a variation, the resuspension container includes at least 3 sterile connectors. The sterile connectors may provide for sterilely connecting the cryopreservation container to the resuspension container such that the contents of the resuspension container may be sterilely transferred to the cryopreservation container. In a variation, the resuspension container may include sterile connectors 116 which permit sterile welding of tubing for fluid transfers and/or connections for aseptic filling of fluids. In a variation, the sterile connectors are DMSO compatible. Non-limiting examples of sterile connectors include N/F valves and non-venting valves. The resuspension container may have a volume sufficient to hold a desired amount of resuspension solution for transfusion. In a variation, the resuspension container may have a volume of less than or equal to 15 mL. In a variation, the resuspension container may have a volume of at least 15 mL. In a variation, the resuspension container may have a volume of at least 30 mL. In a variation, the resuspension container may have a volume of at least 50 mL. In a variation, the resuspension container may have a volume of at least 100 mL. In a variation, the resuspension container may have a volume of at least 500 mL. In a variation, the resuspension container may have a volume of at least 1000 mL.

The resuspension solution may be any biocompatible solution sufficient to be mixed with the body fluid for introduction into the body. In a variation, the resuspension solution is a validated, transfusable solution. Non-limiting examples of transfusable solutions include sterile NaCl, human plasma, and a platelet storage solution. In one variation, the resuspension solution is 0.9% NaCl. In some variations, the sterile resuspension solution is added to the resuspension container either with a sterile connection or through a sterile filling operation in a controlled environment. In other variations, the resuspension container is filled followed by a terminal sterilization by steam, gamma, ebeam, etc.

The container system 100 further includes a connection tube 110 sterilely connecting the cryopreservation container and the resuspension container. The connection tube is configured to withstand being clamped and frozen, e.g. at −80° C. In a variation, the connection tube may be DMSO compatible. The connection tube may include but is not limited to EVA, PVC, or combinations thereof. In one variation, the connection tube is a co-extruded PVC/EVA tube. The connection tube may be sterile welded to any sterile connectors or attachments.

The connection tube has a length sufficient to store the cryopreservation container and the resuspension container in the connected state. In a variation, the length of the connection tube is at least 5 cm. In a variation, the length of the connection tube is at least 10 cm. In a variation, the length of the connection tube is at least 15 cm. In a variation, the length of the connection tube is at least 20 cm. In a variation, the length of the connection tube is at least 25 cm. In a variation, the length of the connection tube is at least 30 cm. In a variation, the length of the connection tube is at least 40 cm. In a variation, the length of the connection tube is at least 50 cm. In other variations, the length of the connection tube is less than or equal to 5 cm. In other variations, the length of the connection tube is less than or equal to 10 cm. In other variations, the length of the connection tube is less than or equal to 15 cm. In other variations, the length of the connection tube is less than or equal to 20 cm. In other variations, the length of the connection tube is less than or equal to 25 cm. In other variations, the length of the connection tube is less than or equal to 30 cm. In other variations, the length of the connection tube is less than or equal to 40 cm. In other variations, the length of the connection tube is less than or equal to 50 cm. In one variation, the connection tube is 19 cm in length. In other variations, the connection tube may have multiple segments or be split with a Y-adapter 112. For example, a first section of the connection tube may be connected to a sterile connector on the cryopreservation container at a first end and connected to a Y-adapter at a second end. A second section of connection tube may be connected to one branch of the Y-adapter at a first end and connected to a sterile connector on the resuspension container at a second end. The first and second sections of the connection tube may be made of different materials.

The container system 100 further includes at least one shut-off element 114 actively associated with the connection tube. The shut-off element is configured to remain in the closed position when frozen, e.g. at −80° C. In a variation, the shut-off element may be a clamp, valve (e.g., stop cock), breakable fitting (frangible), or other appropriate fitting that will allow sterile opening of the tubing between the containers for fluid transfer. In one example, the shut-off element is a roller clamp. The shut-off element is configured to separate the contents of the cryopreservation container and the resuspension container when in the off position and allow mixing of the contents in the open position. In a variation, the container system is frozen and the shut-off element is closed such that the body fluid in a cryopreservation liquid and resuspension solution cannot mix. In another variation, the frozen container system is thawed, the shut-off element is opened, and at least a portion of the resuspension solution is added to the cryopreservation container.

The container system may be frozen in the sterilely connected state until the body fluid is needed to be thawed and transfused. The sterilely connected state includes the cryopreservation container and the resuspension container connected with the connection tube. In some variations, the container system is frozen at a temperature of less than or equal to −15° C. to at least −196° C. In a variation, the container system is frozen to a temperature of less than or equal to −15° C. In a variation, the container system is frozen to a temperature of less than or equal to −25° C. In a variation, the container system is frozen to a temperature of less than or equal to −50° C. In a variation, the container system is frozen to a temperature of less than or equal to −65° C. In a variation, the container system is frozen to a temperature of less than or equal to −70° C. In a variation, the container system is frozen to a temperature of less than or equal to −75° C. In a variation, the container system is frozen to a temperature of less than or equal to −80° C. In a variation, the container system is frozen to a temperature of less than or equal to −100° C. In a variation, the container system is frozen to a temperature of less than or equal to −150° C. In a variation, the container system is frozen to a temperature of less than or equal to −196° C. In one variation, the container system is frozen by placing it in a cardboard plasma freezing container, freezing it in a chest-type mechanical freezer set at −80° C., and holding it frozen at −65° C. The container system may be frozen for up to 2 to up to 10 years depending on the body fluid.

Figure 3:
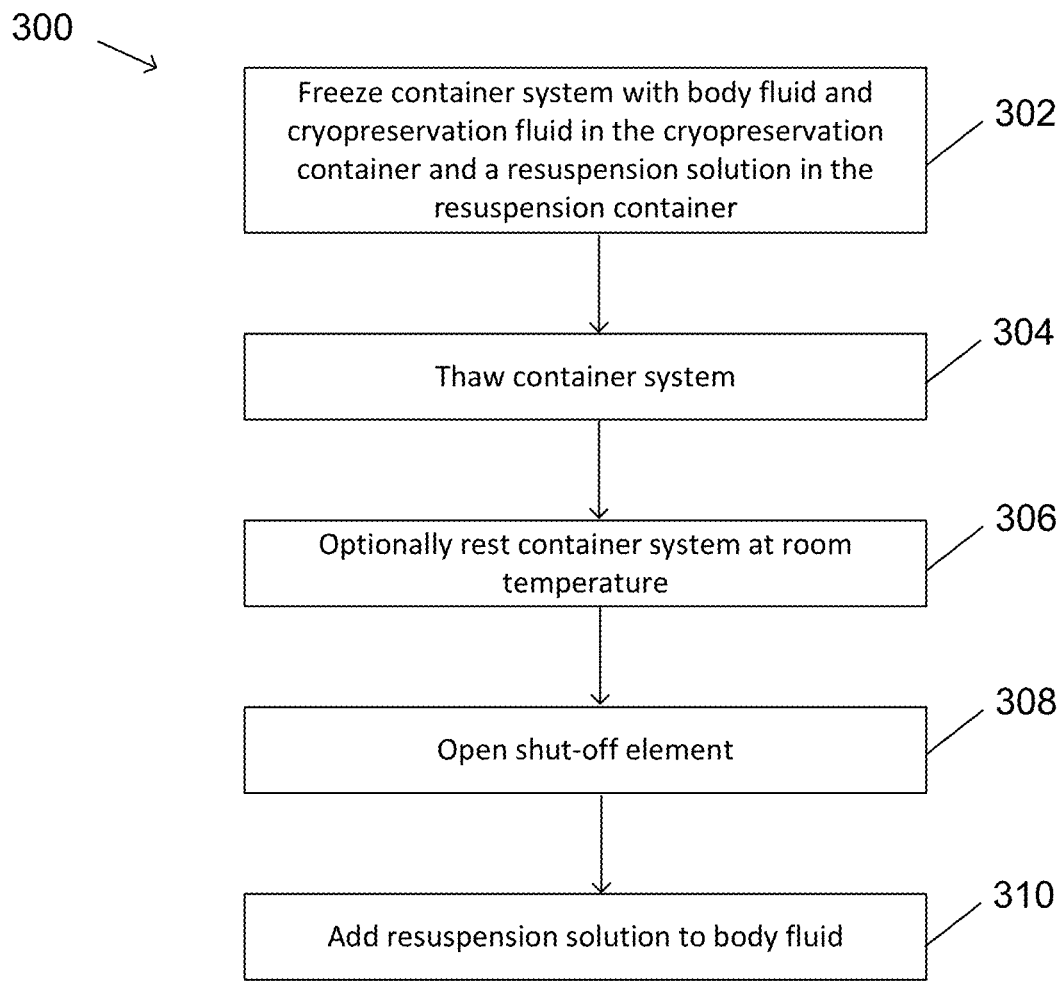
FIG. 3 is a block diagram for a method of preparing a frozen body fluid in the container system of FIG. 1.

FIG. 3 provides a method 300 of preparing a frozen body fluid for transfusion into a patient. The method may include freezing the container system at step 302, thawing the contents of both the cryopreservation container and the resuspension container at step 304, opening the shut-off element at step 308, and mixing a portion of the resuspension solution into the body fluid at step 310. Thawing can be with conductive or radiant heat with or without simultaneous mixing. Methods of thawing include, but are not limited to water baths or microwave heating. In an example, frozen CPP are prepared for transfusion by thawing in a 30-37° C. water bath and resuspended in a resuspension solution. In a variation, the resuspension solution is sterile 0.9% NaCl for infusion or plasma. The resuspension solution is added at a validated time period following thawing, which may be immediately or after an extended rest of the system. The method may optionally include a rest period of up to 30 minutes at room temperature at step 306 after thawing and before adding the resuspension solution. The need for the rest period may be based on the selection of the resuspension solution.

After the contents of the containers are combined, the connection tubing is sealed with a radio frequency sealer, heat sealer, or clamp. The final product may be held under appropriate conditions and/or transported until the time of transfusion that will not be limited due to a breach of the closed system. It may be limited based on other biological and physiochemical features of the final product such as temperature, cell concentration in the bag, the final resuspension solution, gas permeability of the container and others.

In a variation, the thawed, resuspended body fluid has a shelf life of more than 4 hours. In a variation, the resuspended body fluid has a shelf life of at least 4 hours. In a variation, the resuspended body fluid has a shelf life of at least 12 hours. In a variation, the resuspended body fluid has a shelf life of at least 24 hours. In a variation, the resuspended body fluid has a shelf life of at least 2 days. In a variation, the resuspended body fluid has a shelf life of at least 5 days. In a variation, the resuspended body fluid has a shelf life of at least 2 weeks. In a variation, the resuspended body fluid has a shelf life of at least 1 month. In a variation, the resuspended body fluid has a shelf life of at least 2 months. In a variation, the resuspended body fluid has a shelf life of at least 3 months. In some variations, expiry of the resuspended body fluid may be a function of the resuspension solution type, volume of the resuspended body fluid, the content of the body fluid, etc.

Container System with Integrated Sterile Filter

Provided herein is a sterile container system for the cryopreservation and resuspension of a body fluid with an integrated sterile filter. Referring to FIG. 2, the container system 200 includes a cryopreservation container 202 and a sterile filter 214 sterilely and fluidly connected to the cryopreservation container. The cryopreservation container 202 may contain the body fluid in a cryopreservation liquid. In a variation, the sterile filter 214 is connected to the cryopreservation container 202 prior to freezing the cryopreservation container. In a variation, the container system 200 may further include a resuspension container 204 configured to connect to the sterile filter 214. The resuspension container 204 may contain a resuspension solution. The resuspension container may or may not be frozen. The resuspension container may or may not be pre-attached or frozen with the cryopreservation container. In a variation, the connection from the resuspension container to the sterile filter may be with another device (solution administration set) or may be integrally attached to the resuspension container. For example, the resuspension container may connect to the sterile filter via a luer connection. In another variation, the sterile filter may be configured with a sterile dockable piece of tubing on the distal port from cryopreservation container allowing a sterile connection to the filter.

The system includes a sterile filter pre-attached to a cryopreservation or freezing container prior to freezing such that a closed container system is available to thaw and prepare a body fluid product for administration/transfusion. The container system is prepared dry and sterilized by any manner of validated methods including but not limited to ethylene oxide, electron beam, gamma irradiation to form a sterile assembly.

The cryopreservation container 202 may be any container capable of holding a frozen body fluid. The cryopreservation container may be pliable or rigid. Non-limiting examples of materials that may compose the cryopreservation container include EVA, PVC, PTFE, polyolefin polymers, such as polyethylene, and combinations thereof. In one variation, the cryopreservation container may be a cryopreservation bag. The cryopreservation bag is compatible with a cryopreservation fluid. For example, the cryopreservation bag is DMSO compatible. In a variation, the cryopreservation container may be an ethyl vinyl acetate (EVA) freezing bag.

The cryopreservation container 202 may have one or more sterile connectors 206 fluidly connected to the container. In a variation, the cryopreservation container includes at least 1 sterile connector. In a variation, the cryopreservation container includes at least 2 sterile connectors. In a variation, the cryopreservation container includes at least 3 sterile connectors. The sterile connectors 206 may provide for sterilely connecting other containers to the cryopreservation container such that the contents of one container may be sterilely transferred to another container. The sterile connectors permit sterile welding of tubing for fluid transfers and/or connections for aseptic filling of fluids. In a variation, the sterile connectors are DMSO compatible. The cryopreservation container may have a volume sufficient to hold a desired amount of body fluid for transfusion. In a variation, the cryopreservation container may have a volume of at least 1 mL. In a variation, the cryopreservation container may have a volume of at least 5 mL. In a variation, the cryopreservation container may have a volume of at least 10 mL. In a variation, the cryopreservation container may have a volume of at least 25 mL. In a variation, the cryopreservation container may have a volume of at least 200 mL. In a variation, the cryopreservation container may have a volume of at least 500 mL. In a variation, the cryopreservation container may have a volume of at least 800 mL. In a variation, the cryopreservation container may have a volume of at least 1000 mL.

The cryopreservation container contains a body fluid in a cryopreservation liquid. Non-limiting examples of body fluids that may be contained within the cryopreservation container include platelets, whole blood, red blood cells, plasma, cord blood, stem cells, mesenchymal stromal/stem cells, other biologicals, and combinations thereof. The body fluid may be human or animal body fluid for use in humans or animals. In one variation, the body fluid is platelets in plasma that have been collected from healthy volunteer allogeneic donors. In a variation, the collected platelets may be irradiated with 25Gy.

In a variation, the body fluid is combined with a cryopreservation fluid in the cryopreservation container. The cryopreservation fluid may be added to the body fluid aseptically in a clean room (e.g., ISO 5 classified) or using sterile welding of a cryopreservation fluid container to the cryopreservation container containing the body fluid. Examples of the cryopreservation fluid include DMSO, glycerol, or any fluid capable of preserving a frozen body fluid, such as a cell freezing medium. In one variation, the cryopreservation fluid is 27% DMSO. In one variation, the body fluid mixture is DMSO cryopreserved platelets (CPP). The cryopreservation fluid may be added such that it is 3% to 10% by volume of the total mixture. In a variation, the cryopreservation fluid may be at least 3% by volume of the mixture with the body fluid. In a variation, the cryopreservation fluid may be at least 6% by volume of the mixture with the body fluid. In a variation, the cryopreservation fluid may be at least 8% by volume of the mixture with the body fluid. In a variation, the cryopreservation fluid may be at least 10% by volume of the mixture with the body fluid. In another variation, the cryopreservation fluid may be less than or equal to 3% by volume of the mixture with the body fluid. In another variation, the cryopreservation fluid may be less than or equal to 6% by volume of the mixture with the body fluid. In another variation, the cryopreservation fluid may be less than or equal to 8% by volume of the mixture with the body fluid. In another variation, the cryopreservation fluid may be less than or equal to 10% by volume of the mixture with the body fluid.

After the cryopreservation fluid is added to the body fluid, the mixture may be concentrated within the cryopreservation bag, such as by centrifugation. The supernatant may then be removed from the cryopreservation bag so that the volume of the body fluid mixture in the cryopreservation bag is less than the starting volume of the body fluid and cryopreservation fluid. In a variation, the volume of concentrated body fluid mixture to be frozen is at least 1 mL. In a variation, the volume of concentrated body fluid mixture to be frozen is at least 5 mL. In a variation, the volume of concentrated body fluid mixture to be frozen is at least 10 mL. In a variation, the volume of concentrated body fluid mixture to be frozen is at least 15 mL. In a variation, the volume of concentrated body fluid mixture to be frozen is at least 20 mL. In a variation, the volume of concentrated body fluid mixture to be frozen is at least 25 mL. In a variation, the volume of concentrated body fluid mixture to be frozen is at least 35 mL. In a variation, the volume of concentrated body fluid mixture to be frozen is at least 50 mL. In a variation, the volume of concentrated body fluid mixture to be frozen is at least 100 mL. In other variations the volume of concentrated body fluid mixture to be frozen is less than or equal to 20 mL. In other variations the volume of concentrated body fluid mixture to be frozen is less than or equal to 25 mL. In other variations the volume of concentrated body fluid mixture to be frozen is less than or equal to 35 mL. In other variations the volume of concentrated body fluid mixture to be frozen is less than or equal to 50 mL. In other variations the volume of concentrated body fluid mixture to be frozen is or less than or equal to 100 mL. For example, platelets may be concentrated to 20 mL to 35 mL by centrifugation in the cryopreservation container.

The container system 200 further includes a sterile filter 214 sterilely connected to the cryopreservation container 202. The sterile filter 214 is configured to sterilely filter any fluid, such as a resuspension solution that is added to the cryopreservation container. In an example, the sterile filter 214 has a pore size of less than or equal to 0.22 μm. In one variation, the sterile filter has ultrafiltration cutoff of 0.1 μm. The sterile filter 214 may be a membrane filter (non-woven, woven or other means of making holes in a membrane of less than 0.22 μm) or a semipermeable dialysis type membrane. In a variation, the sterile filter is integrated with the cryopreservation container. The sterile filter 214 may be connected to a sterile connector 206 on the cryopreservation container or connected to a connection tube 210 that is fluidly connected to the sterile connector. The sterile filter is integrated with the cryopreservation container such that the connection remains sterile throughout the freezing and thawing processes. The sterile filter is capable of being frozen down to at least −80° C. or at least −196° C. without impacting the functionality of the filter once thawed. In a variation, the sterile filter may have a Leur connection for connecting the resuspension container to the sterile filter.

In some variations, the connection tube 210 may have multiple segments or be split with a Y-adapter 212. For example, a first section of the connection tube may be connected to a sterile connector on the cryopreservation container at a first end and connected to a Y-adapter at a second end. A second section of connection tube may be connected to one branch of the Y-adapter at a first end and connected to a sterile filter at a second end. The first and second sections of the connection tube may be made of different materials. In another variation, the sterile filter may be directly connected to a branch of the Y-adapter.

The container system 200 may further include at least one shut-off element 213 actively associated with the connection tube or Y-adapter. The shut-off element is configured to remain in the closed position when frozen, e.g. at −80° C. In a variation, the shut-off element may be a clamp, valve (e.g., stop cock), breakable fitting (frangible), or other appropriate fitting that will allow sterile opening of the tubing between the cryopreservation container and sterile filter for fluid transfer. In one example, the shut-off element is a roller clamp. The shut-off element is configured to prevent the contents of the cryopreservation container from entering the sterile filter when in the off position and allow passage of the resuspension solution in the open position. In a variation, the container system is frozen and the shut-off element is closed such that the body fluid in a cryopreservation liquid cannot reach the sterile filter. In another variation, the frozen container system is thawed, the shut-off element is opened, and at least a portion of the resuspension solution is added to the cryopreservation container through the sterile filter.

The container system 200 further includes a resuspension container 204 having a resuspension solution contained within the resuspension container. The resuspension container may be any container capable of being frozen. The resuspension container may be pliable or rigid. Non-limiting examples of materials that may compose the resuspension container include EVA, PVC, PTFE, polyolefin polymers, such as polyethylene, and combinations thereof. In one variation, the resuspension container may be a bag. In another variation, the resuspension container is a syringe. The resuspension container may be compatible with the cryopreservation fluid. For example, the resuspension container is DMSO compatible. In a variation, the cryopreservation container may be an EVA freezing bag.

The resuspension solution may be any biocompatible solution sufficient to be mixed with the body fluid for introduction into the body. In a variation, the resuspension solution is a verified, transfusable solution. Non-limiting examples of transfusable solutions include sterile NaCl, human plasma, and a platelet storage solution. In one variation, the resuspension solution is 0.9% NaCl. In some variations, the sterile resuspension solution is added to the resuspension container either with a sterile connection or through a sterile filling operation in a controlled environment. In other variations, the resuspension container is filled followed by a terminal sterilization by steam, gamma, ebeam, etc.

The resuspension container 204 may have one or more sterile connectors 208 fluidly connected to the container. In a variation, the resuspension container includes at least 1 sterile connector. In a variation, the resuspension container includes at least 2 sterile connectors. In a variation, the resuspension container includes at least 3 sterile connectors. The sterile connectors may provide for sterilely connecting the resuspension container to the sterile filter 214 such that the contents of the resuspension container may be sterilely transferred to the cryopreservation container. In a variation, the resuspension container may include sterile connectors 216 which permit sterile welding of tubing for fluid transfers and/or connections for aseptic filling of fluids. In a variation, the sterile connectors are DMSO compatible. Non-limiting examples of sterile connectors include N/F valves and non-venting valves. The resuspension container may have a volume sufficient to hold a desired amount of resuspension solution for transfusion. In a variation, the resuspension container may have a volume of less than or equal to 15 mL. In a variation, the resuspension container may have a volume of at least 15 mL. In a variation, the resuspension container may have a volume of at least 30 mL. In a variation, the resuspension container may have a volume of at least 50 mL. In a variation, the resuspension container may have a volume of at least 100 mL.

In a variation, the sterile connector 208 of the resuspension container 204 may be connected to a connection tube, which is then connected to the sterile filter 214. In a variation, the connection tube may be DMSO compatible. The connection tube may include but is not limited to EVA, PVC, or combinations thereof. In one variation, the connection tube is a co-extruded PVC/EVA tube. The connection tube may be sterile welded to any sterile connectors or attachments.

In a variation, the length of the connection tube is at least 5 cm. In a variation, the length of the connection tube is at least 10 cm. In a variation, the length of the connection tube is at least 15 cm. In a variation, the length of the connection tube is at least 20 cm. In a variation, the length of the connection tube is at least 25 cm. In a variation, the length of the connection tube is at least 30 cm. In a variation, the length of the connection tube is at least 40 cm. In a variation, the length of the connection tube is at least 50 cm. In other variations, the length of the connection tube is less than or equal to 5 cm. In other variations, the length of the connection tube is less than or equal to 10 cm. In other variations, the length of the connection tube is less than or equal to 15 cm. In other variations, the length of the connection tube is less than or equal to 20 cm. In other variations, the length of the connection tube is less than or equal to 25 cm. In other variations, the length of the connection tube is less than or equal to 30 cm. In other variations, the length of the connection tube is less than or equal to 40 cm. In other variations, the length of the connection tube is less than or equal to 50 cm. In one variation, the connection tube is 19 cm in length.

The container system may be frozen in the sterilely connected state until the body fluid is needed to be thawed and transfused. The sterilely connected state includes the cryopreservation container with the integrated sterile filter. In some variations, the container system is frozen at a temperature of less than or equal to −15° C. to at least −196° C. In a variation, the container system is frozen to a temperature of less than or equal to −15° C. In a variation, the container system is frozen to a temperature of less than or equal to −25° C. In a variation, the container system is frozen to a temperature of less than or equal to −50° C. In a variation, the container system is frozen to a temperature of less than or equal to −65° C. In a variation, the container system is frozen to a temperature of less than or equal to −70° C. In a variation, the container system is frozen to a temperature of less than or equal to −75° C. In a variation, the container system is frozen to a temperature of less than or equal to −80° C. In a variation, the container system is frozen to a temperature of less than or equal to −100° C. In a variation, the container system is frozen to a temperature of less than or equal to −150° C. In a variation, the container system is frozen to a temperature of less than or equal to −196° C. In one variation, the container system is frozen by placing it in a cardboard plasma freezing container, freezing it in a chest-type mechanical freezer set at −80° C., and holding it frozen at −65° C. The container system may be frozen for up to 2 to up to 10 years depending on the body fluid.

Figure 4:
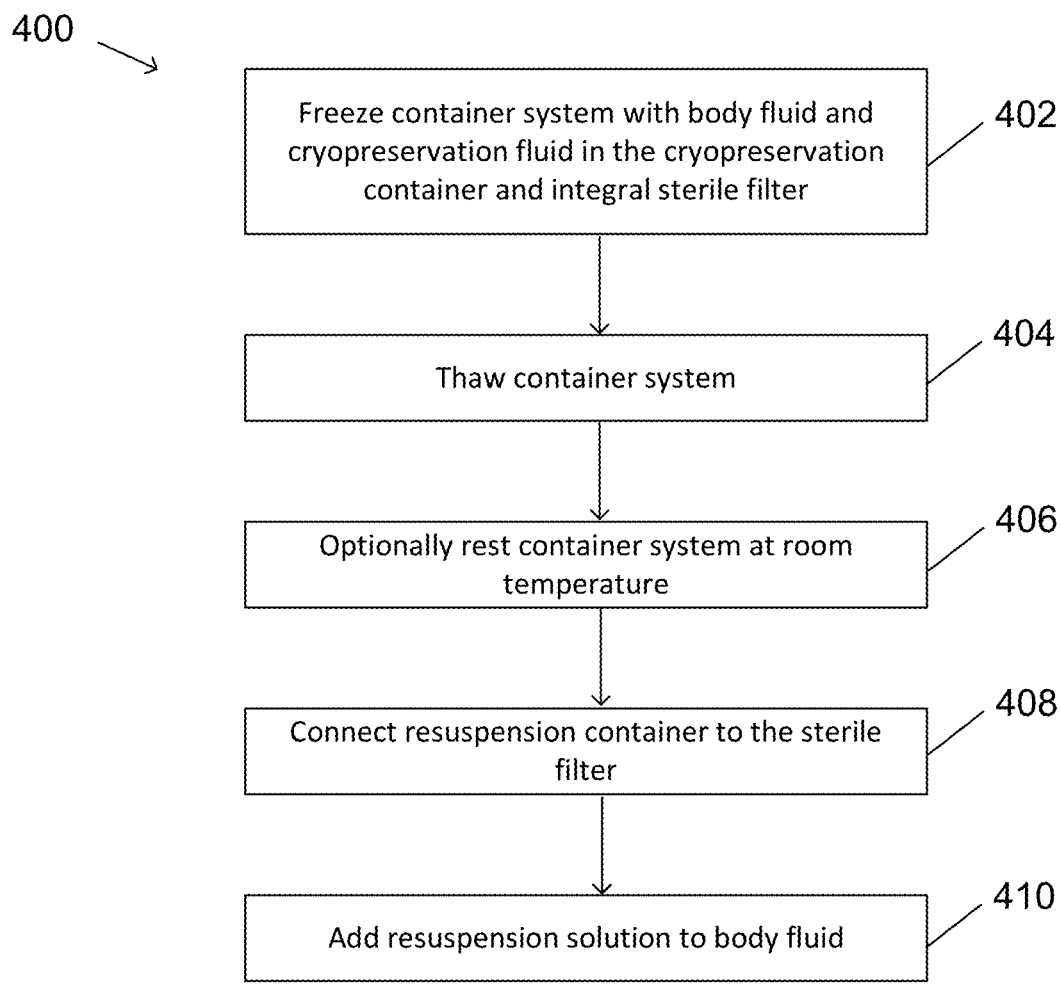
FIG. 4 is a block diagram for a method of preparing a frozen body fluid in the container system of FIG. 2.

FIG. 4 provides a method 400 of preparing a frozen body fluid for transfusion into a patient. The method may include freezing the container system at step 402, thawing the contents of both the cryopreservation container and the resuspension container at step 404, connecting the resuspension container to the sterile filter at step 408, and mixing a portion of the resuspension solution into the body fluid at step 410. Thawing can be with conductive or radiant heat with or without simultaneous mixing. Methods of thawing include, but are not limited to water baths or microwave heating. In an example, frozen CPP are prepared for transfusion by thawing in a 30-37° C. water bath and resuspending in a resuspension solution. In a variation, the resuspension solution is sterile 0.9% NaCl for infusion or plasma. The resuspension solution is added at a validated time period following thawing, which may be immediately or after an extended rest of the system. The method may optionally include a rest period of up to 30 minutes at room temperature at step 406 after thawing and before adding the resuspension solution. The need for the rest period may be based on the selection of the resuspension solution.

After the contents of the containers are combined, the connection tubing is sealed with a radio frequency sealer, heat sealer, or clamp. The final product may be held under appropriate conditions and/or transported until the time of transfusion that will not be limited due to a breach of the closed system. It may be limited based on other biological and physiochemical features of the final product such as temperature, cell concentration in the bag, the final resuspension solution, gas permeability of the container and others.

In a variation, the thawed, resuspended body fluid has a shelf life of more than 4 hours. In a variation, the resuspended body fluid has a shelf life of at least 4 hours. In a variation, the resuspended body fluid has a shelf life of at least 12 hours. In a variation, the resuspended body fluid has a shelf life of at least 24 hours. In a variation, the resuspended body fluid has a shelf life of at least 2 days. In a variation, the resuspended body fluid has a shelf life of at least 5 days. In a variation, the resuspended body fluid has a shelf life of at least 2 weeks. In a variation, the resuspended body fluid has a shelf life of at least 1 month. In a variation, the resuspended body fluid has a shelf life of at least 2 months. In a variation, the resuspended body fluid has a shelf life of at least 3 months. In a variation, expiry of the resuspended body fluid may be a function of the resuspension solution type, volume of the resuspended body fluid, the content of the body fluid, etc.

Having described several variations, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed variations teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A closed and sterile container device comprising:
   a cryopreservation container comprising a body fluid in a cryopreservation liquid;
   a resuspension container comprising a resuspension solution;
   a connection tube sterilely connecting the cryopreservation container and the resuspension container; and
   a single shut-off element actively associated with the connection tube,
   wherein the cryopreservation container and the resuspension container remain sterilely connected and the shut-off element is closed such that the body fluid in the cryopreservation liquid and the resuspension solution can be kept separate when the container system is frozen, and
   wherein the cryopreservation container and the resuspension container remain sterilely connected and the shut-off element is opened such that the body fluid in the cryopreservation liquid and the resuspension solution sterilely mix after thawing.

2. The container device of claim 1, wherein the body fluid is selected from platelets and blood.

3. The container device of claim 2, wherein the body fluid is cryopreserved platelets.

4. The container device of claim 1, wherein the connection tube is DMSO compatible.

5. The container device of claim 1, wherein when the frozen container system is thawed, the shut-off element is opened, and at least a portion of the resuspension solution is added to the cryopreservation container, creating a resuspended body fluid product.

6. The container device of claim 5, wherein the resuspended body fluid product remains shelf stable for more than 4 hours.

7. The container device of claim 1, wherein the resuspension solution is a transfusable solution.

8. The container device of claim 7, wherein the transfusable solution is selected from sterile NaCl, human plasma, and a platelet storage solution.

9. The container device of claim 6, wherein the resuspended body fluid product remains shelf stable for up to at least 14 days.

10. The container device of claim 1, wherein the cryopreservation container is an ethyl vinyl acetate (EVA) freezing bag.

11. The container device of claim 1, wherein the connection tube and shut-off element are configured to withstand being clamped and frozen at −80° C.

* * * * *